United States Patent [19]

Chen

[11] Patent Number: 4,735,570

[45] Date of Patent: Apr. 5, 1988

[54] FALSE TOOTH ATTACHMENT

[76] Inventor: Tan S. Chen, No. 198, Nan-Tai Road, Shan-Ming Chu, Kaohsiung, Taiwan

[21] Appl. No.: 6,361

[22] Filed: Jan. 23, 1987

[51] Int. Cl.⁴ .............................................. A61C 13/10
[52] U.S. Cl. .................... 433/191; 433/177; 433/181
[58] Field of Search ............... 433/191, 192, 193, 194, 433/195, 180, 181, 182, 183, 177, 178

[56] References Cited

U.S. PATENT DOCUMENTS

| | | | |
|---|---|---|---|
| 1,671,781 | 5/1928 | Phillips | 433/183 |
| 2,826,814 | 3/1958 | Sappey et al. | 433/193 |
| 3,834,023 | 9/1974 | Lapeyre | 433/177 |

FOREIGN PATENT DOCUMENTS

471005  5/1952  Italy ..................................... 433/177

*Primary Examiner*—John J. Wilson
*Attorney, Agent, or Firm*—Morton J. Rosenberg

[57] ABSTRACT

This invention relates to a false tooth attachment and in particular to one including a fixed member having a side plate and an engaging end, a front retainer made of a resilient metal wire bent into a shaped of an inverted letter V engageable with the engaging end, and a rear retainer formed of a resilient metal wire shaped into a letter U having two legs spaced apart by a distance equal to that between two recesses of the engaging end, whereby the false tooth can be easily removed from a supporting tooth simply by pushing a long leg of the front retainer.

1 Claim, 8 Drawing Sheets

PRIOR ART

PRIOR ART

FIG . 7

FALSE TOOTH ATTACHMENT

BACKGROUND OF THE INVENTION

Figure 4:
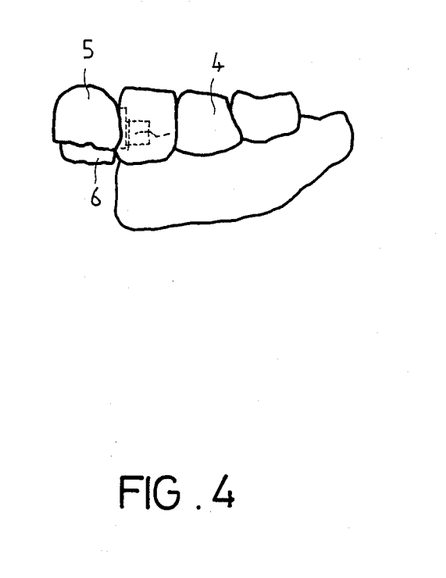
FIG. 4 is a working view of the false tooth attachment.
Figure 5:
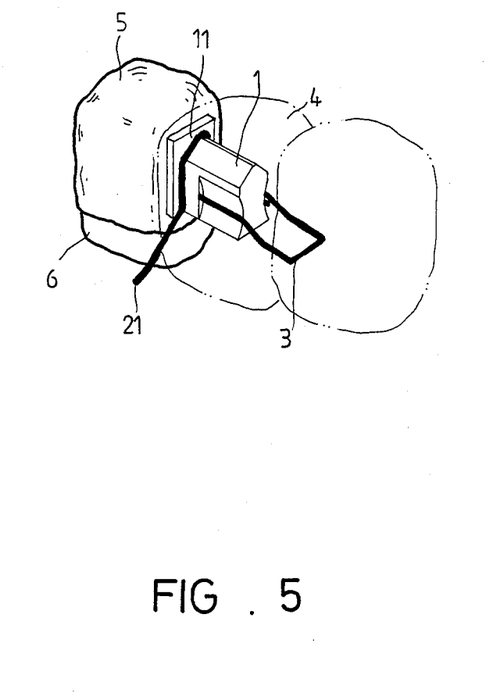
FIG. 5 is a perspective enlarged view of the false tooth attachment shown in FIG. 4.
Figure 6:
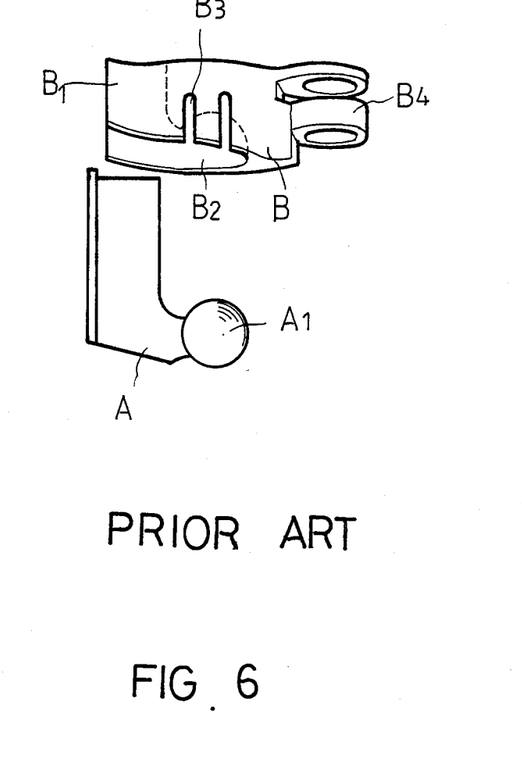
FIG. 6 shows a prior art false tooth attachment.
Figure 7:
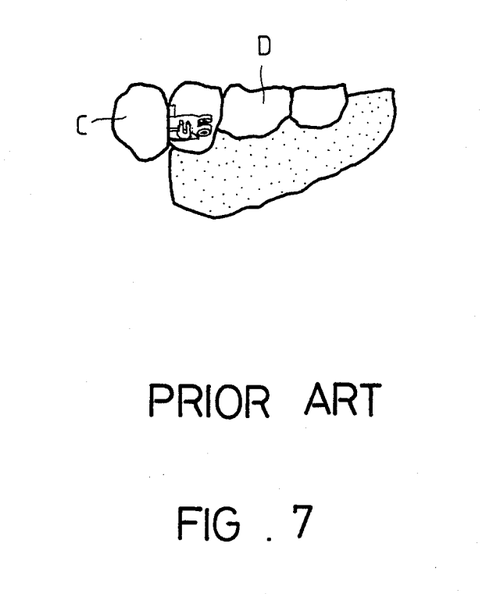
FIG. 7 is a working view of the prior art false tooth attachment.
Figure 8:
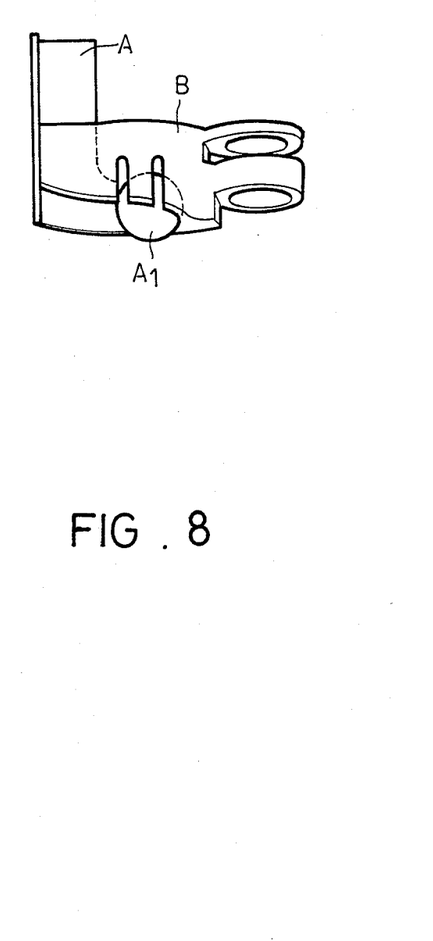
FIG. 8 is an enlarged perspective of the false tooth attachment shown in FIG. 7.

The false tooth attachment is a requisite in mounting the false tooth in the gums of the teeth. With reference to FIG. 4, there is shown a prior art false tooth attachment which comprises a fixed member A and an engaging member B. The fixed member A is a L-shaped body with a ball A1 at its lower end, while the engaging member B is provided with two arms B1 for receiving the fixed member A. The rear end of the engaging member B has a spherical recess B2 and two slots B3 for holding the ball A1 of the fixed member A. As illustrated in FIG. 5, the fixed member A is then fused or welded to a supporting tooth C and its rear end B4 is enclosed by a false tooth D. Hence, by means of the connection between the engaging member B and the fixed member A, the false tooth D can be firmly mounted on the gum of the teeth and easily removed for cleaning.

It should be noted that compactness, sturdiness and low cost are three targets pursued by the manufacturer of the false tooth. However, as stated above, the prior art false tooth attachment is composed of rather complicated component parts and so it has a large size. Further, part of the prior art attachment will extend out of the false tooth particularly when it is applied to the front teeth of the lower jaw since the front teeth are smaller in size and toc large to be enclosed by the false tooth. Moreover, the assembly of the prior art attachment is achieved by the engagement between the ball A1 and the spherical recess B2 thereby causing stress concentration in the neck of the ball A1 and therefore, easily breaking the engaging member B. In addition, the connection between the engaging member B and the fixed member A must be of high accuracy and this will increase the manufacturing cost thereof.

It is, therefore, an object of the present invention to provide an improved false tooth attachment which may obviate and mitigate the above-mentioned drawbacks.

SUMMARY OF THE INVENTION

This invention relates to an improved false tooth attachment.

It is the primary object of the present invention to provide a false tooth attachment the volume of which is only 3/5 of the prior art.

It is another object of the present invention to provide a false tooth attachment which can be entirely enclosed by the false tooth.

It is still another object of the present invention to provide a false tooth attachment which can be applied to the front teeth of the lower jaw.

It is still another object of the present invention to provide a false tooth attachment which has long service life.

It is a further object of the present invention to provide a false tooth attachment which is inexpensive to manufacture.

Other objects and merits and a fuller understanding of the present invention will be obtaiend by those having ordinary skill in the art when read in conjunction with the accompanying drawings wherein like numerals refer to like or similar parts and in which:

DETAILED DESCRIPTION OF THE PREFERRED EMBODIMENT

Figure 1:
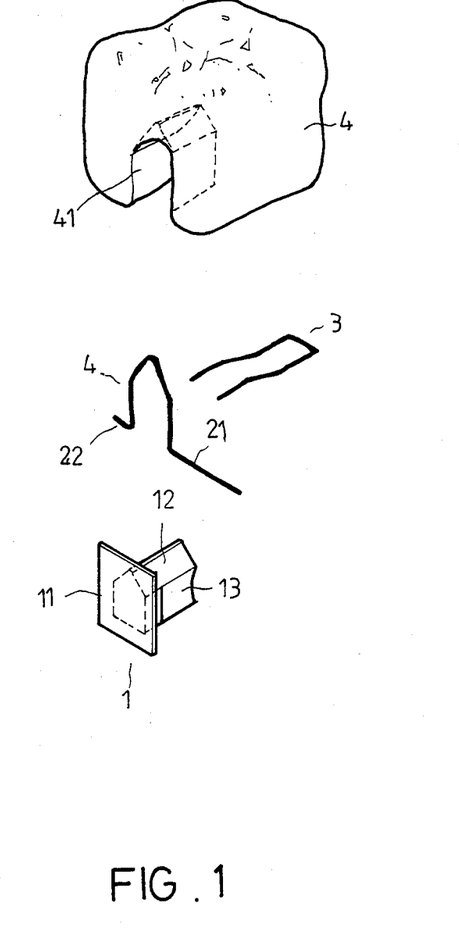
FIG. 1 is an exploded view of the present invention.

With reference to FIG. 1, the false tooth attachment according to the present invention mainly comprises a fixed member 1, a front retainer 2 and a rear retainer 3. The fixed member 1 is provided with a side plate 11 at one end and an engaging end 12 at its top. The top of the engaging end 12 is shaped into an inverted letter V while both sides thereof have a curved recess 13 with a length at least equal to one-half of the length of the engaging end 12.

The front retainer 2 is made of a resilient metal wire bent into an inverted letter V and can just be inserted on the rear part of the engaging end 12. The front retainer 2 has two legs 21 and 22; the leg 21 is longer than the leg 22. The short leg 22 is entirely enclosed by the resin of the false tooth, while the long leg 21 extends a little bit out of the false tooth for pushing.

The rear retainer 3 is also made of a resilient metal wire bent into a shape of a letter U. The opening of the rear retainer 3 is approximately equal to the width between the two recesses 13 of the engaging end 12. From the side view of the ear retainer 3, it first extends horizontally, then inclined downwards and extends horizontally again. The bending seam of the rear retainer 3 is used as a limit point for mounting into the false tooth and provide stronger construction.

Figure 2:
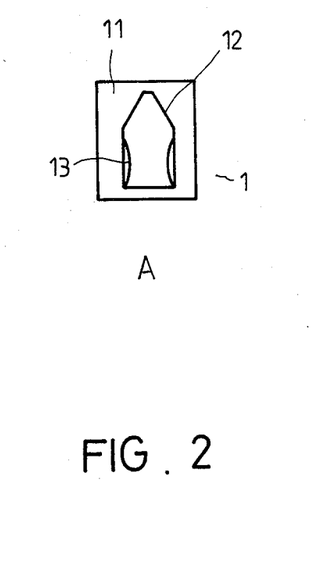
FIG. 2 is a rear elevational view of the fixed member of the present invention.

Referring to FIG. 2, the front retainer 2 and the rear retainer 3 are disposed into the false tooth 4. The false tooth 4 has in its interior a recess with a open bottom adapted to receive the engaging end 12 of the fixed member 1. The front retainer 2 is mounted in the front part of the recess 41 and enclosed by the resin of the false tooth with its long leg 21 extending a little bit out of the surface of the false tooth. The rear attachment 3 is disposed in the rear end of the recess 41 for engaging with the curved recess 13 of the engaging end 12. The rear portion of the rear attachment 3 is embedded into the false tooth 4 and only part of the rear attachment 3 extends out of the recess 13 so as to engage with the curved recess 13.

Figure 3:
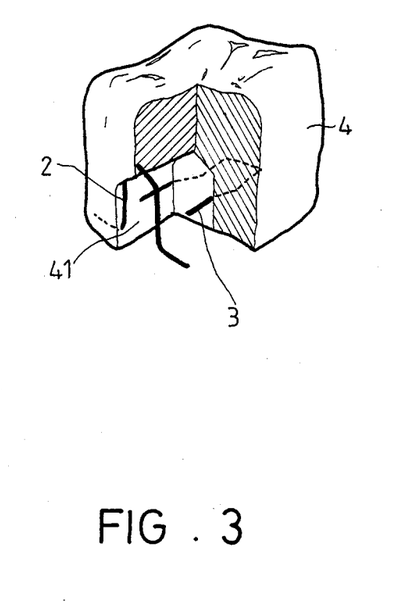
FIG. 3 is a cutaway view of the false tooth attachment of the present invention.

FIG. 3 shows the working of the present invention. As illustrated, the side plate 11 of the fixed member 1 is fixedly attached on a supporting tooth 5. The supporting tooth 5 is put on to a tooth 6. When desired to mount the false tooth on the gum of the teeth, simply put the false tooth 4 on the fixed member 1 with the engaging end 14 of the fixed member 1 received in the recess 41 of the false tooth 4. Meanwhile, the front retainer 2 clamps the rear portion of the engaging end 12 while the two arms of the rear retainer 3 are guided into the recess 13. As a result, the false tooth 4 can be firmly mounted. When desired to detach the false tooth 4, it is only necessary to push the long leg 21 of the front retainer 2 so that the front retainer 2 and the rear retainer 3 will separate from the engaging end 12 and the curved recess 13 thereby detaching the false teeth from the supporting tooth 5.

Although this invention has been described with a certain degree of particularity, it is understood that the present disclosure is made by way of example only and that numerous changes in the detail of construction and the arrangement and combination of parts may be resorted to without departing from the scope and spirit of the invention as hereinafter claimed.

I claim:

1. A false tooth attachment comprising:
   a fixed member having a side plate and an engaging end, the side plate being designed to fixedly attach to a supporting tooth for attaching on to a normal tooth, said engaging end having an inverted V-shaped top and a curved recess at both vertical sides thereof, said curved recess having a length at least equal to one-half of length of said engaging end;
   a front retainer made of a resilient metal wire bent into a shape of an inverted letter V, said front retainer being designed so as to be able to just fit on a rear portion of the engaging end and embedded into a false tooth, said front retainer having a short leg entirely enclosed by the false tooth and a long leg extending a little bit out of surface of the false tooth; and
   a rear retainer made of a resilient metal wire bent into a shape of a letter U, said rear retainer having two legs spaced apart by a distance approximately equal to that between the two recesses of the engaging end, said rear retainer being designed so that it first extends horizontally, then inclined downwards and extends horizontally again;
   whereby the false tooth can be easily removed removed from a supporting tooth simply by pushing the longleg of the front retainer.

* * * * *